United States Patent
Hermans et al.

(10) Patent No.: US 10,597,339 B2
(45) Date of Patent: Mar. 24, 2020

(54) METHOD FOR CHIRAL RESOLUTION AND DEVICE THEREFOR

(71) Applicants: UNIVERSITÉ DE STRASBOURG, Strasbourg (FR); CENTRE NATIONAL DE LA RECHERCHE SCIENTIFIQUE—CNRS, Paris (FR)

(72) Inventors: Thomas Marinus Hermans, Strasbourg (FR); Akihiro Sato, Strasbourg (FR); Vincent Marichez, Strasbourg (FR)

(73) Assignees: Universite de Strasbourg, Strasbourg (FR); Centre National de la Recherche Scientifique—CNRS, Paris (FR)

( * ) Notice: Subject to any disclaimer, the term of this patent is extended or adjusted under 35 U.S.C. 154(b) by 0 days.

(21) Appl. No.: 15/501,674

(22) PCT Filed: Aug. 7, 2015

(86) PCT No.: PCT/EP2015/068273
§ 371 (c)(1),
(2) Date: Feb. 3, 2017

(87) PCT Pub. No.: WO2016/020532
PCT Pub. Date: Feb. 11, 2016

(65) Prior Publication Data
US 2017/0226027 A1 Aug. 10, 2017

(30) Foreign Application Priority Data

Aug. 8, 2014 (EP) .................................. 14306261

(51) Int. Cl.
*B03C 1/32* (2006.01)
*C07B 57/00* (2006.01)
(Continued)

(52) U.S. Cl.
CPC .............. *C07B 57/00* (2013.01); *B03C 1/023* (2013.01); *B03C 5/02* (2013.01); *C01B 33/18* (2013.01); *C07B 59/00* (2013.01); *C07C 51/42* (2013.01)

(58) Field of Classification Search
CPC .. B03C 1/023; B03C 1/32; B03C 5/02; B03C 2201/18; C07B 57/00; C07C 51/42; C01B 32/172; C01B 32/215
See application file for complete search history.

(56) References Cited

U.S. PATENT DOCUMENTS

| | | | | |
|---|---|---|---|---|
| 4,900,421 A | * | 2/1990 | Grutzner | B01D 57/02 204/450 |
| 5,738,792 A | * | 4/1998 | Schoendorfer | A61M 1/3496 210/321.63 |
| 5,888,748 A | * | 3/1999 | Crabb | G01N 33/56905 435/29 |
| 6,099,730 A | * | 8/2000 | Ameer | A61M 1/16 210/321.67 |

(Continued)

FOREIGN PATENT DOCUMENTS

| | | | | |
|---|---|---|---|---|
| JP | 2005145887 A | * | 6/2005 | |
| WO | WO 2004/037301 A2 | | 6/2004 | |
| WO | WO-2017003909 A3 | * | 2/2017 | ............ C07B 57/00 |

OTHER PUBLICATIONS

Marcos, et al, "Separation of Microscale Chiral Objects by Shear Flow"; Physical Review Letters; vol. 102, No. 15; Apr. 1, 2009.

*Primary Examiner* — Joseph C Rodriguez
(74) *Attorney, Agent, or Firm* — Morgan, Lewis & Bockius LLP

(57) ABSTRACT

A method is described for chiral resolution of chiral species contained in a liquid placed in a cell formed by an inner wall and an outer wall surrounding the inner wall over at least a portion of the inner wall, where each of the outer and inner walls are a solid of revolution about a longitudinal axis and (Continued)

are coaxial to one another, where the method comprises rotating the outer wall in one direction of rotation with respect to the inner wall for generating a Taylor-Couette flow within the liquid; collecting at least one of the chiral species.

8 Claims, 6 Drawing Sheets

(51) Int. Cl.
*C07B 59/00* (2006.01)
*B03C 1/023* (2006.01)
*B03C 5/02* (2006.01)
*C01B 33/18* (2006.01)
*C07C 51/42* (2006.01)

(56) References Cited

U.S. PATENT DOCUMENTS

| | | | | |
|---|---|---|---|---|
| 6,344,121 B1* | 2/2002 | Stalcup | ............... | B01D 57/02 |
| | | | | 204/450 |
| 7,425,265 B2* | 9/2008 | Schoendorfer | ...... | B01D 29/117 |
| | | | | 210/321.63 |
| 7,459,121 B2* | 12/2008 | Liang | ............... | B01D 67/0046 |
| | | | | 210/650 |
| 7,935,906 B2* | 5/2011 | Kibar | ............... | B03C 1/24 |
| | | | | 209/127.1 |
| 9,308,172 B2* | 4/2016 | Lee | ............... | A61K 9/1647 |
| 9,926,201 B1* | 3/2018 | Kessler | ............... | C01B 31/0273 |
| 2013/0046086 A1* | 2/2013 | Lustig | ............... | B03C 5/02 |
| | | | | 536/25.41 |
| 2014/0166545 A1* | 6/2014 | Lyding | ............... | B03C 1/023 |
| | | | | 209/212 |

* cited by examiner

METHOD FOR CHIRAL RESOLUTION AND DEVICE THEREFOR

TECHNICAL FIELD

The present invention relates to the technical field of chiral resolution of chiral species, for example separation of two species from one another, or the extraction of one or more chiral species dissolved or dispersed in an achiral liquid or mixture. More in particular, the present invention relates to a method for chiral resolution of chiral species and a device for chiral resolution of chiral species.

PRIOR ART

The, sometimes dramatic, discovery of different pharmacological activity for chiral molecules that are enantiomers of each other has resulted in the necessity of asymmetric synthesis or chiral resolution of the distinct enantiomers from one another so that they can be administered as isolated compounds (eutomers). Thus, asymmetric synthesis and chiral resolution are two of the most important processes in the pharmaceutical industry, as well as in other industrial sectors such as food, petroleum, agrochemicals and biochemistry.

Asymmetric synthesis and chiral resolution commonly rely on the use of a third chiral compound.

Asymmetric synthesis, also called chiral synthesis or enantioselective synthesis, consists of a chemical reaction or reaction sequence in which one or more new elements of chirality are formed in a substrate molecule and which produces the stereoisomeric (in the present invention: enantiomeric) products in unequal amounts, or more simply put into words the synthesis of a compound by a method that favours the formation of a specific stereoisomer over the others.

Asymmetric synthesis of some compounds can be difficult to develop and requires sometime laborious research. Furthermore, many times it still requires chiral resolution because although the formation of the desired stereoisomer is favoured, other stereoisomers can still be present in the product mixture and must be separated from the desired one.

Chiral resolution is commonly performed by chiral column chromatography. In the case of enantiomers, such a method usually consists in making a mixture comprising the enantiomers to be separated to flow through a column filled with a substrate comprising one or more third chiral compounds used as chiral stationary phase(s) and by washing the chiral stationary phase(s) with a solvent after the enantiomers have been introduced into the column. The third chiral compound(s) will selectively retain one or more of the enantiomer, thus leading to the formation of different portions of the eluate, each having a differentiated concentration of the different enantiomers. Thus, portions with higher concentration of one enantiomers and substantially null concentration of the others are obtained. Sometime some portions need to be further eluted in another column to complete the chiral resolution.

One drawback of chiral column chromatography is the high consumption of solvent. Another drawback is the cost of the third compounds used for the chiral stationary phases.

In the late 90's, a few reports mentioned an already centenary, but no less exciting idea: the possibility to discriminate chiral objects using hydrodynamic flows as alternative to chiral column chromatography. The idea that fluid flows could induce chiral resolution was initially suggested by Howard et al., "The hydrodynamic resolution of optical isomers", in *AIChE Journal*, 22, 794-798 (1976). Since then, this idea has been theoretically examined in considerable detail. Achieving chiral resolution of enantiomers without the use of any chiral stationary phase (the most costly component in chiral column chromatography) would revolutionise the pharmaceutical industry. However, there is still no agreement on the magnitudes or even directions of forces exerted by fluid flows onto chiral objects. Whereas several experimental studies report chirality-specific flow effects, on scales ranging from molecular (porphyrin aggregation during rotary evaporation), through microscopic (helical bacteria), these studies largely remain phenomenological. In some cases the fluid flows are implemented by using imprecise systems such as rotary evaporators or magnetic stirrers, for which the flow structure on different length-scales is largely unknown.

Flow types that have been most studied are Hagen-Poiseuille flow and Couette flow.

One of such studies using Couette flow was conducted by Makino and Doi, reported in *Physics of fluids*, 17, 103605 (2005), in an article entitled "Migration of twisted ribbon-like particles in simple shear flow". In their simulation, Makino and Doi used a model of twisted ribbons, in lieu of chiral molecules, in a liquid subjected to a simple shear flow generated between coaxial inner and outer cylinders when the inner cylinder is rotated. They predicted that a large Péclet number is needed to get an efficient chiral resolution. Also, they concluded that the migration velocity of the enantiomers is extremely small for small Péclet numbers.

Other authors such as Marcos et al., in *Physical Review Letters*, 102, 158103 (2009) in an article entitled "Separation of microscale chiral objects by shear flow" tried Hagen-Poiseuille flow for chiral resolution. In their experiment, they applied a shear flow in a micrometre-sized channel formed by four walls, in which nonmotile, right-handed, helically shaped bacteria *Leptospira biflexa* flaB mutant were placed. These bacteria were on average 16 μm long, 150 nm thick and have an average diameter of 200 nm.

However, Marcos et al. method requires a considerable amount of solvent. Specifically, since the channel width is 1 mm, and the injection point is 100 μm, the mixture is diluted ten times by the solvent. Further, this method requires high pressure pumps to achieve high shear rates, and it is believed that it would be difficult to scale up this method to industrial sizes. In addition, this method merely achieves enrichment (of about 80%) of the chiral objects, and not full chiral resolution. Finally, the different enantiomers would need to be collected in the four quadrants of the channel cross section (i.e., one enantiomer will move to the top left and bottom right of the channel, and the other enantiomer will move to the top right and bottom left of the channel). This means that the already small channel must be split into four smaller channels to collect the enantiomers, leading again to a large pressure drop and poor scalability.

Thus, an efficient method for chiral resolution is still needed.

SUMMARY OF THE INVENTION

One objective of the present invention is to overcome at least one drawback of the prior art as identified here above.

To this aim, the present invention provides a method for chiral resolution of chiral species contained in a liquid placed in a cell formed by an inner cylinder and an outer cylinder, the outer and inner cylinder being coaxial to one another, the method comprising:

rotating the outer cylinder in one direction of rotation with respect to the inner cylinder for generating a Taylor-Couette flow within the liquid;

collecting at least one of the chiral species.

Contrary to the prediction of the prior art, the inventors have surprisingly found out that using Taylor-Couette flow generated accordingly to the invention enables the chiral resolution not only of system with large Péclet number, but also those with small Péclet number. Indeed, the inventors discovered that for small Péclet number, the migration velocity of the species was at least one order of magnitude higher than what Makino and Doi predicted.

Further, rotating the outer cylinder instead of the inner one prevents any possible Taylor instabilities at high rotation velocities.

Other optional and non-limiting features are as follows.

The method may additionally comprise collecting at least one of the other chiral species.

The method may additionally or alternatively comprise rotating the inner wall in the same or opposite direction as the outer wall.

The liquid may additionally or alternatively have a viscosity of $5 \times 10^{-5}$ Pa·s to $10^3$ Pa·s The shear rate created within the gap may additionally or alternatively be in average 1 s$^{-1}$ to $10^{12}$ s$^{-1}$.

The method may additionally or alternatively comprise applying an electric field within the liquid.

The method may additionally or alternatively comprise applying a magnetic electric field within the liquid.

The method may additionally or alternatively comprise controlling the temperature within the cell.

According to another aspect, the invention also provides a device for chiral resolution of chiral species contained in a same liquid, comprising a cell with an inner cylinder and an outer cylinder coaxial to the inner cylinder and forming with the inner cylinder a gap for receiving the liquid;

an actuator for rotating the outer cylinder in one direction of rotation so that in operation a Taylor-Couette flow is generated within the liquid;

a collector for collecting at least one of the chiral species.

Optional and non-limiting features of the device are as follows.

The device may additionally comprise another collector for collecting the other of the chiral species.

The device may additionally or alternatively comprise another actuator for rotating the inner wall in in the same or opposite direction than the outer wall.

The outer wall may additionally or alternatively comprise a first end section, and the end of the inner wall closer to the first end section of the outer wall does not extend up to the first end section of the outer wall.

The device may additionally or alternatively comprise an electric field generator for generating an electric field within the gap. The electric field can be oscillating or constant. An electric field gradient can also be applied to the electric field.

The device may additionally or alternatively comprise a magnetic field generator for generating a magnetic field within the gap. The magnetic field can be oscillating or constant. A magnetic field gradient can also be applied to the electric field.

The device may additionally or alternatively comprise a temperature controller for controlling the temperature within the cell.

DRAWINGS

Other objectives, features and advantages will be described hereafter with reference to the following illustrative and non-limiting figures.

DESCRIPTION OF THE INVENTION

Figure 1:
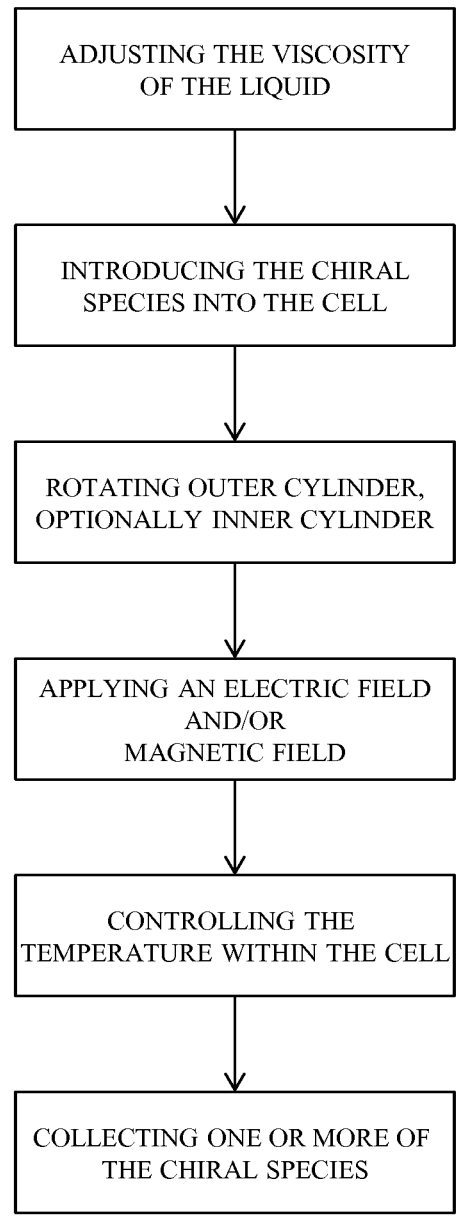
FIG. 1 is a flow chart illustrating the steps of the method for chiral resolution of the invention.

With reference to FIG. 1, a method for chiral resolution of chiral species according to the invention is now described in more details.

Figure 7:
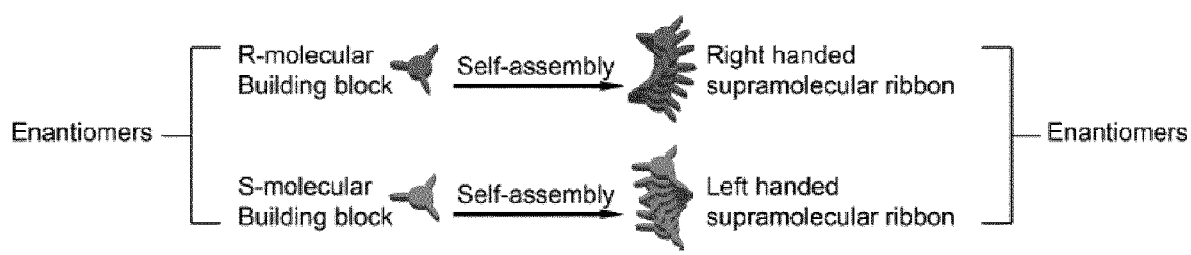
FIG. 7 illustrates self-assembling chiral species.

By "species" it is meant any objects of nanometre to micrometre size such as micrometre-sized twisted ribbons or helices, or nanometre-sized particles and molecules. A species can also be a supramolecular assembly, i.e. an assembly of building blocks, the building blocks being able to assemble with one another forming the supramolecular assembly. The building blocks may be chiral. The verb "self-assemble" is used here to mean that the chiral building blocks naturally have the ability to assemble with one another or that this ability is induced. The supramolecular assembly exhibits a chirality that can be intrinsic, induced or enhanced. "Intrinsically chiral supramolecular assembly" means that the building blocks form a chiral supramolecular assembly. "Enhanced chiral supramolecular assembly" means an intrinsically chiral supramolecular assembly the chirality of which can be made stronger upon influence of one or more condition of the chiral resolution method, for example by the flow to which they are subjected (flow-enhanced chiral supramolecular assembly). "Induced chiral supramolecular assembly" means that the building blocks form an achiral supramolecular assembly, but this achiral supramolecular assembly becomes chiral upon influence of one or more conditions of the chiral resolution method, for example by the flow to which they are subjected (flow-induced chiral supramolecular assembly). Thus, the building blocks can be more efficiently separated with the present invention than when they are not assembled (see FIG. 7). An example of such building block is a molecule, for example a chiral molecule, which is optionally bound to a gemini surfactant.

A "chiral species" is a species that cannot be superimposed to its own mirror-image. Two chiral species that are mirror-images of one other are said to be "enantiomorphic" to one another; together, they are referred to by the terms "a pair of enantiomorphic species". The meaning of "enantiomorphic" encompasses that of "enantiomeric" such as enantiomers, which is a chiral molecule that is not superposable to its own mirror-image.

Such a method for chiral resolution makes it possible to separate two chiral species of a same set of enantiomorphic species contained in a same liquid placed in a cell. This method can also be used to separate the chiral species of a plurality of sets of enantiomorphic species from one another. This method can still be used to separate one or more chiral species from an achiral medium or mixture.

The cell is formed by an inner wall and an outer wall that are coaxial to one another. The outer wall surrounds the inner wall over at least a portion of the inner wall along its length. In other words, the inner and outer walls longitudinally overlap over a certain length along the common longitudinal axis of the walls. The chiral resolution will be obtained substantially within the cylinders' overlap.

The method comprises:
rotating the outer wall in one direction of rotation with respect to the inner wall for generating a Taylor-Couette flow within the liquid;
collecting at least one of the chiral species.

In the past, it was believed that for small particles, a high Péclet number was needed to have efficient chiral resolution. The Péclet number Pe is a dimensionless number defined as follows:

$$Pe = \frac{\dot{\gamma}}{D_r}$$

$$D_r = \frac{k_B T}{f_r}$$

wherein $\dot{\gamma}$ represent the shear rate that is applied and $D_r$ the rotational diffusion constant of the species. The rotation diffusion scales linearly with temperature T ($k_B$ is the Boltzmann constant), and depends on the friction coefficient $f_r$ of the species. The friction coefficient $f_r$ depends on the liquid in which the species is placed, and the shape, size and chirality of the enantiomorph.

Thus, if the Péclet number is small, diffusion would take over the motion of the species to separate induced by the liquid flow and the distribution of each species along the separation direction would be wide. Thus, it was expected in the past that for small particles such as chiral molecules, an excessively high shear rate was needed.

Figure 8:
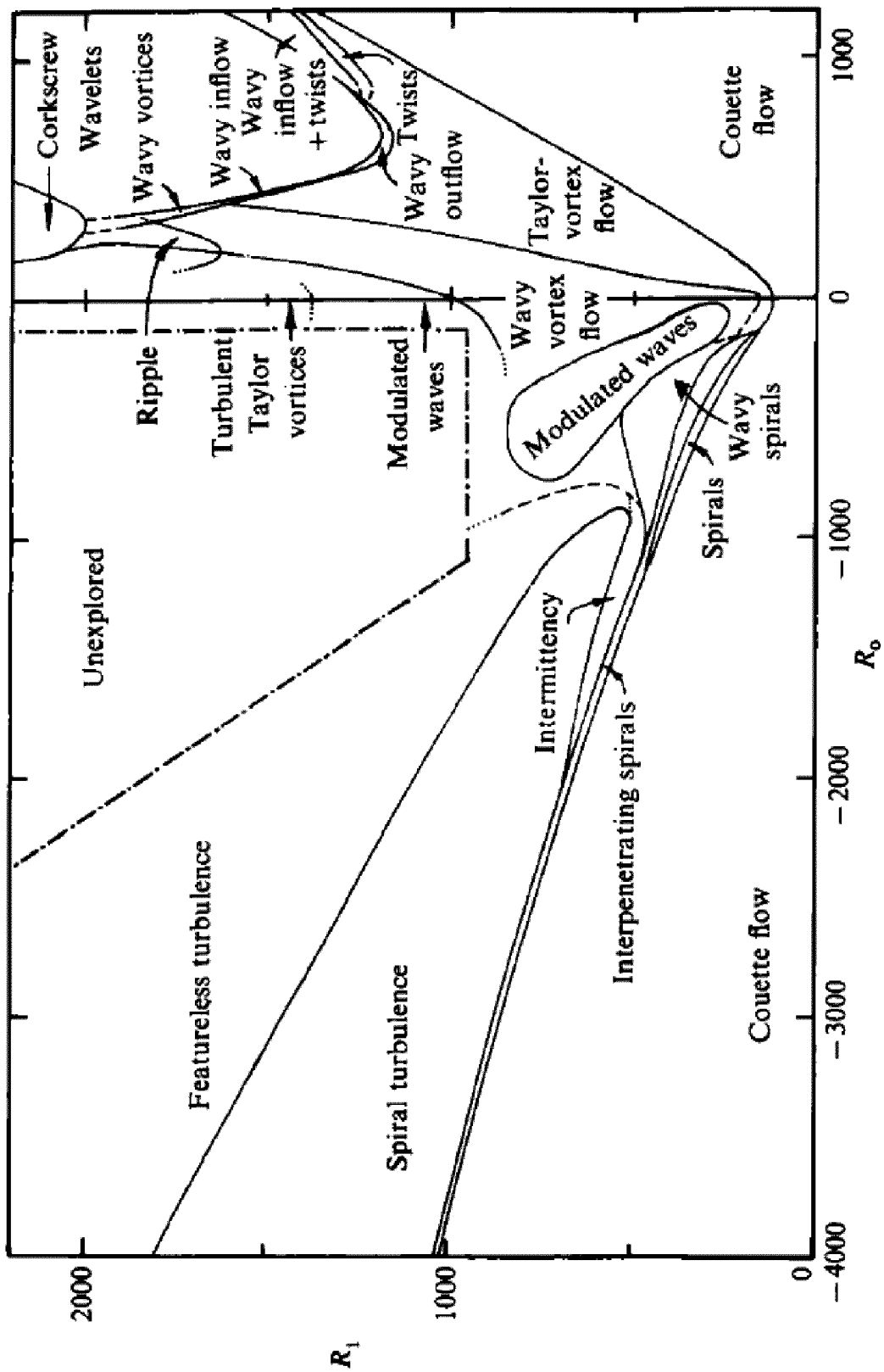
FIG. 8 is a diagram showing the different flow types corresponding to a Taylor-Couette flow.
Figure 9:
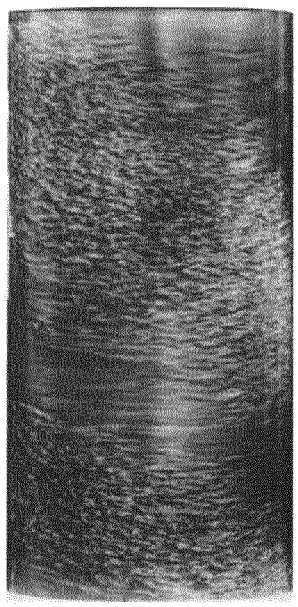
FIGS. 9 through 12 are photographs of four exemplified flow types corresponding to a Taylor-Couette flow.
Figure 10:
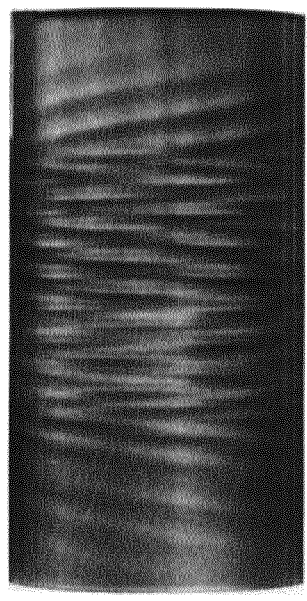
Figure 11:
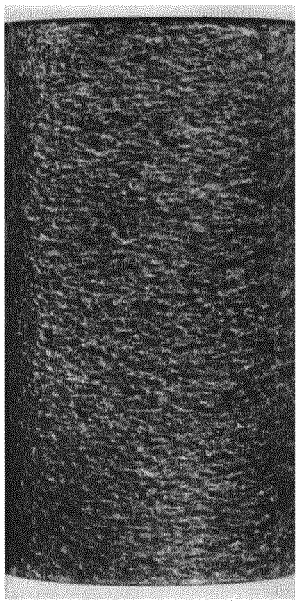
Figure 12:
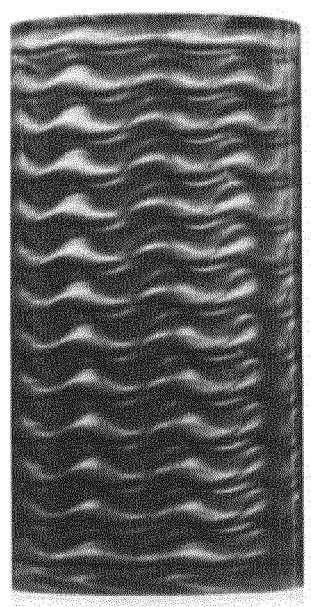

A Taylor-Couette flow is defined by physicists as a flow obtained by rotating two coaxial cylinders with respect to one another. Many types of fluid flows can be generated by such a Taylor-Couette flow, such as a circular Couette flow, helical flow (especially when the liquid comprising the chiral species is continuously introduced in the gap between the inner wall and the outer wall from one end of the cell formed by the cylinders and retrieved from the other end as described herebelow), stable or unstable low Reynolds number flow, stable or unstable high Reynolds number flow, etc. FIG. 8 shows flow examples that can be obtained with a Taylor-Couette flow and FIGS. 9 to 12 show photographs of four examples of such flows: spiral turbulence, interpenetrating spirals, featureless turbulence, and modulated wavy vortices respectively. The flow type typically depends on the Reynold's numbers Re computed with respect to the outer and inner wall:

$$Re_o = \omega_o R_o G v^{-1} \text{ and } Re_i = \omega_i R_i G v^{-1}$$

with $\omega_o$ the rotation velocity of the outer cylinder, $R_o$ the radius of the inner face of the outer cylinder, $\omega_i$ the rotation velocity of the inner cylinder, $R_i$ the radius of the outer face of the inner cylinder, G the gap between the two cylinder (i.e., $R_o$-$R_i$), and v the kinematic viscosity.

However, as already mentioned, the inventors found out that using Taylor-Couette flow generated accordingly to the invention enables the chiral resolution not only of systems with large Péclet number, but also those with small Péclet number without necessitating applying an excessively high shear rate.

Figure 2:
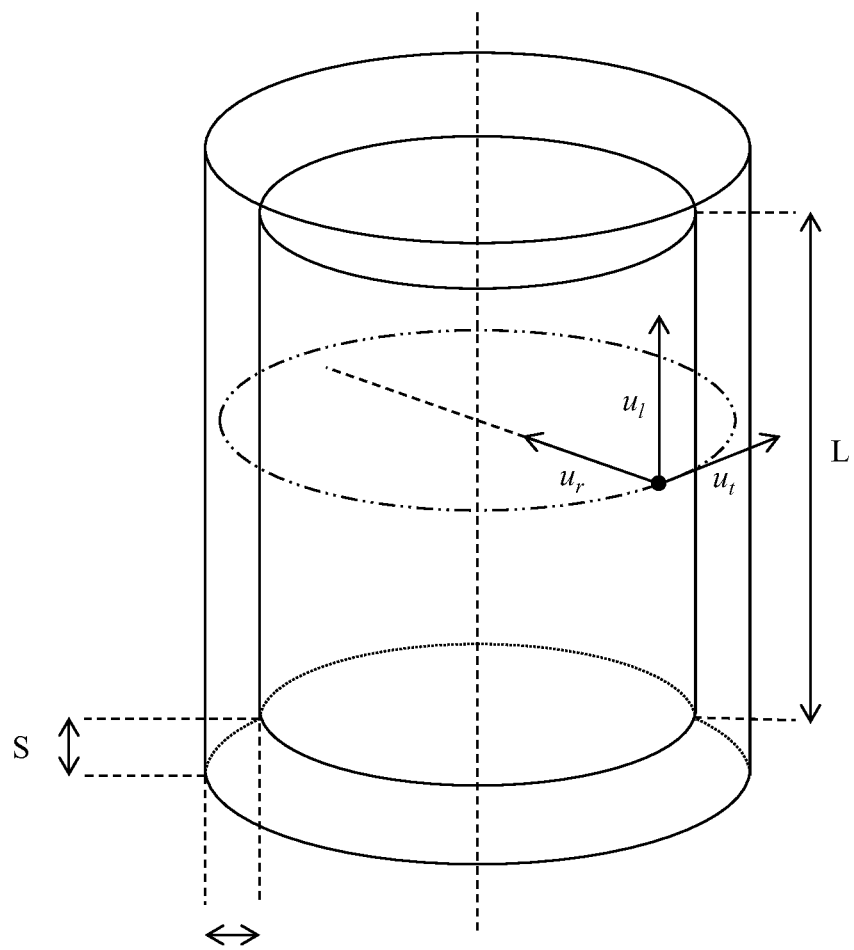
FIG. 2 is an illustration showing a cell with cylindrical inner and outer walls, and the shifts experienced by the chiral species.

Upon the application of a Taylor-Couette flow, in addition to a tangential motion $u_t$, the chiral species experience forces collinear to the rotation vector and will react differently thereto with one chiral species of a set of enantiomorphic species shifting along a first direction $u_l$ collinear to the longitudinal axis of the cylinders and the other chiral species of the set of enantiomorphic species shifting along a second direction opposite to the first direction (see FIG. 2). In addition to the collinear forces, the inventors have discovered that the chiral species also experience forces that are perpendicular to the rotation vector: the chiral species also experience a radial shift $U_r$. A moment after the establishment of the Taylor-Couette flow, the chiral species stabilise, each at different "orbits", i.e. different positions along the radius. The mean radii for each chiral species depend on the species' chirality but not on their initial positions (see FIG. 2). This radial shift $u_r$ can be advantageously used to separate chiral species that experience a strong shift as further detailed below.

The rotation of the outer wall is maintained until sufficient separation between chiral species.

The liquid comprising the chiral species can be introduced in the gap between the inner wall and the outer wall as a single batch before rotating one or both cylinders. The liquid can also be introduced in a plurality of batches with the rotation of the cylinder(s) being stopped or maintained before introducing the next batch. The liquid can finally be introduced continually.

Alternatively, the chiral species may be introduced in the gap between the inner and outer walls and the liquid introduced later. The chiral species will then be dissolved or dispersed in situ.

It is possible to collect only one of the chiral species, for example when only one of the species is of particular interest; the other is discarded. This can also be the case when only one chiral species of a set of enantiomorphic species is of particular interest. It is also possible to collect more than one chiral species, particularly both chiral species of a set of enantiomorphic species. In this latter case, both enantiomorphic species can be collected at the same time.

In addition, collection of the chiral species can be done at many different points along the length of the inner or outer walls, as to collect fractions of the same chiral species or different chiral species if they need to be separated simultaneously.

The collection can be carried out by applying externally a negative pressure to one or more outlets of the cell, thus causing liquid to be removed from the cell. Different negative pressures can be applied to different outlets if the cell is equipped with more than one outlet. Alternatively, a positive pressure can be applied at one or more inlets of the cell, thus causing an equal outflow in all outlets simultaneously (providing that the pressure drop for each outlet is equal). The content of the entire cell can also be extracted through a single outlet and can then be split into fractions containing different chiral species, or chiral species that are similar or of different sizes.

The inner wall is preferably immobile and only the outer wall rotates. However, the inner wall can also be rotated in the same or opposite direction as the outer wall; rotating the walls in opposite directions being beneficial since adsorption of the chiral species on the outer face of the inner wall and on the inner face of the outer wall can be decreased.

The shear rate created by the rotating outer wall, and optionally the inner wall, is advantageously $1 \text{ s}^{-1}$ to $10^{12} \text{ s}^{-1}$, preferably $10^2 \text{ s}^{-1}$ to $10^{10} \text{ s}^{-1}$, more preferably $10^6 \text{ s}^{-1}$ to $10^8 \text{ s}^{-1}$. The shear rate is linked to the rotation velocities of the outer wall and the inner wall as well as the gap width between both walls in the overlap portion thereof:

$$\dot{\gamma} = \frac{R_o^2(R_i^2 + r^2)(\omega_o - \omega_i)}{r^2(R_o^2 - R_i^2)},$$

with $\omega_o$ the rotation velocity of the outer cylinder, $R_o$ the radius of the inner face of the outer cylinder, $\omega_i$ the rotation velocity of the inner cylinder, $R_i$ the radius of the outer face of the inner cylinder, r the position between the inner and outer cylinder.

The rotation velocity of the outer wall is advantageously 1000 rpm to 500000 rpm (rounds per minute) for nanometre-sized chiral species, 1 rpm to 5000 rpm for micrometer-sized chiral species, and 1 rpm to 100 rpm for sub-millimetre-sized chiral species.

The rotation velocity of the inner wall is advantageously 0 rpm to 20000 rpm. However, the rotation of the inner wall should be such that the critical Taylor number of approximately 1700, for example about 1708, is not exceeded to prevent the formation of instabilities in the flow such as Taylor vortex flow, wavy vortex flow, spiral vortex flow, or turbulent flow.

The liquid containing the species has advantageously a viscosity of $5 \times 10^{-5}$ Pa·s to $10^3$ Pa·s. Preferably, for high Péclet number, the viscosity is $10^{-1}$ Pa·s to $10^3$ Pa·s and for small Péclet number, the viscosity is $5 \times 10^{-5}$ Pa·s to $10^{-1}$ Pa·s A higher viscosity reduces the rotational diffusion, and in this way favours chiral migration over dispersion by diffusion. In addition, the shear stress scales linearly with viscosity, and a higher shear stress leads to a higher chiral lift force, and thus faster separation.

The liquid can be a solvent as for example supercritical $CO_2$, acetone, hexane, dichloromethane, tetrahydrofuran, toluene, chloroform, methanol, p-xylene, benzene, chlorobenzene, cyclohexane, water, ethanol, 1,2-dichlorobenzene, 1,2,4-trichlorobenzene, isopropylalcohol, dimethyl sulfoxide, blood, glycerol, honey, or molten glass (for example at 1000° C. or 600° C.). The viscosity of these solvents can be found in the "CRC Handbook of Chemistry and Physics", 93$^{rd}$ edition, by David E. Lide (CRC Press, 2012).

The higher the viscosity of the liquid, the easier it is to separate the chiral species from one another and especially for nanometre-sized species.

The method may also comprise adjusting the viscosity of the liquid so that a desired value thereof is obtained prior to rotating the outer cylinder, optionally the inner cylinder.

For species with a small Péclet number, i.e. a Péclet number lower than about 5, the chiral resolution can be perfected by applying an aligning electric field within the liquid directed from the outer wall to the inner wall. The chiral species having a dipole moment (for example molecules with a dipole moment) align their dipole moment with the electric field. The voltage is advantageously 0 V to 300 kV, preferably 100 V to 10 kV, still preferably 500 V to 5 kV. The direction of the electric field is preferentially in the radial direction. The electric field can be either constant along the length of the inner and outer walls, or a gradient field can be applied along the length of the inner and outer walls. The electric field can also be an oscillating electric field. Applying a gradient field enables to control the radial position of the chiral species in order to bring at least some of them closer to the outer wall since the shear rate is higher there.

The alignment can also be obtained by applying a constant magnetic field within the gap 4 between the inner and outer walls 2, 3. The chiral species having a magnetic dipole moment (for example paramagnetic molecules) align their magnetic dipole moment with the constant magnetic field. The value of the magnetic field is advantageously 1 mT to 50 T, preferably 100 mT to 5 T, still preferably 500 mT to 2 T. The direction of the constant magnetic field is preferentially in the radial direction. The magnetic field can be either constant along the length of the inner and outer walls, or a secondary gradient field can be applied along the length of the inner and outer walls at the same time as the radial magnetic field. The magnetic field can also be an oscillating magnetic field. Applying a gradient field enables to control the radial position of the chiral species in order to bring at least some of them closer to the outer wall since the shear rate is higher there. When a magnetic field is used, the liquid is preferably a diamagnetic medium for the separation of paramagnetic enantiomorphs, or the liquid is paramagnetic for the separation of diamagnetic enantiomorphs.

Both electric field and magnetic field can be applied at the same time thus generating a Lorentz force that is directed along the longitudinal axis of the cell. When there is only one desired chiral species or when there is a plurality of desired chiral species subjected to chiral lift forces directed in the same direction, both electric field and magnetic field can be adjusted so that the Lorentz force is directed in the same or opposite direction as the chiral lift forces.

The electric field and/or magnetic field make it possible to exploit the radial shift $u_r$ for achieving better chiral resolution.

The method can also comprise controlling the temperature within the cell. For example, by lowering the temperature of the mixture, Brownian motion of the chiral species is reduced. Also, in some cases, such as for water, the viscosity of the liquid in which they are dissolved or dispersed can be increased. Both effects help in increasing the Péclet number, making chiral resolution more efficient. One or both of the inner and outer walls may be heated or cooled.

Although the different steps are describes in a particular order and are represented as sequential steps in FIG. 1, this does not necessarily mean that they are carried out in that particular order. Indeed, the person skilled in the art would understand clearly which steps can be simultaneously performed. For example, each of the following steps can be executed at the same time: rotating the outer wall, rotating the inner wall, applying an electric field. Collecting one or more of the chiral species can be initiated after the start of the rotation of the outer wall, optionally also inner wall, but there can be a period of time when collecting and rotating are both performed.

With reference to FIGS. 3 to 6, a device 1 for chiral resolution according to the invention is described hereafter.

This device 1 enables the separation of chiral species contained in a same liquid. The device 1 can also be used to separate the chiral species of a plurality of sets of enantiomorphic species from one another. This method can still be used to separate one or more chiral species from an achiral medium or mixture in which they are dissolved or dispersed.

The device 1 comprises a cell with:
- an inner wall 2;
- an outer wall 3 coaxial to the inner wall 2 and forming with this latter a gap 4 for receiving the liquid.

Each of the inner wall 2 and the outer wall 3 is a solid of revolution. By "solid of revolution" it is particularly understood in the scope of the present invention that the inner wall 2, respectively the outer wall 3, comprises an outer face 21, respectively an inner face 31, obtained by rotating a plane curve (i.e. a curve that can be contained in a plane) around an axis, which is the longitudinal axis A of the inner wall 2, respectively outer wall 3.

In operation, only the outer face 21 of the inner wall 2 and the inner face 31 of the outer wall 3 are of any interest (and are illustrated in the drawings). Consequently, by stating that the inner and outer walls 2, 3 are coaxial and that they overlap to some degree, it is meant here that the outer face 21 of the inner wall 2 and the inner face 31 of the outer wall 3 are coaxial and that they overlap to some degree. The shape of the inner face, if any, of the inner wall 2 and the shape of the outer face of the outer wall 3 do not matter.

The outer wall 3 surrounds the inner wall 2 over at least a portion of the inner wall 2 along its length. In other words, the inner and outer walls 2, 3 longitudinally overlap over a certain length along their common longitudinal axis A.

The length L of the overlap, taken longitudinally to the longitudinal axis of the inner and outer walls 2, 3 is advantageously greater than 3 times the average size of the gap width G. Actually, the length L of the overlap depends on the migration velocity of the chiral species. The faster the chiral species migrate, the longer the length L of the overlap. Thus, for slow migrating chiral species, the length L should be greater than 3 times the average size of the gap width G; and for fast migrating chiral species, the length can be up to 100 times the average size of the gap width G. The gap width G is measured perpendicularly to the longitudinal axis of the walls.

The cell comprises at least one inlet $1_{in}$ and at least one outlet $1_{out}$. The inlet $1_{in}$ and/or outlet $1_{out}$ can be provided on the inner or/and outer walls 2, 3. Preferably, there is one inlet and a plurality of outlets. Providing a plurality of outlets, and in particular when they are longitudinally distributed, helps in the chiral resolution for obtaining better resolution efficiency as described infra. A plurality of outlets in the inner wall 2 suits best chiral species that migrate more axially than radially, while a plurality of outlets in the outer wall 3 suits best chiral species that migrate more radially than axially.

The inlet(s) $1_{in}$ and/or outlet(s) $1_{out}$ can be independently a through hole, a nozzle, a mesh or a porous membrane formed by the material of the inner or outer wall. For example for chiral species that have a strong radial chiral migration they can be collected through the outer wall, by either placing many outlets on the outer wall or by having a porous outer wall.

Figure 6:
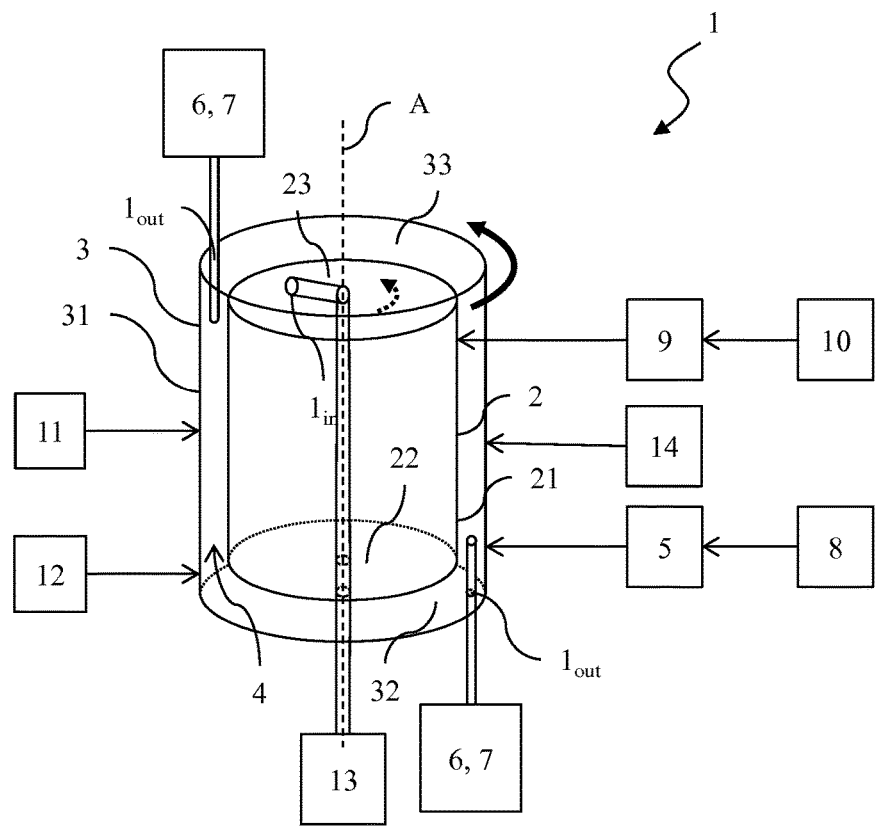
FIG. 6 is a schematic illustration of a device for chiral resolution of the invention and which is adapted to carry out the method, the steps of which are illustrated in FIG. 1.

Both the outer face 21 of the inner wall 2 and the inner face 31 of the outer wall 3 can be cylindrical (see FIGS. 2 and 6). By "cylindrical", it is understood a right circular cylinder, i.e. the cross-section of the cylinder is a circle so that when the outer cylinder rotates, a constant gap is maintained between the outer surface of the inner cylinder and the inner surface of the outer cylinder.

In such case, the inner cylinder 2 comprises an outer diameter smaller than the inner diameter of the outer cylinder 3 and both longitudinally overlap one another over a certain length along their common longitudinal axis A.

Figure 3:
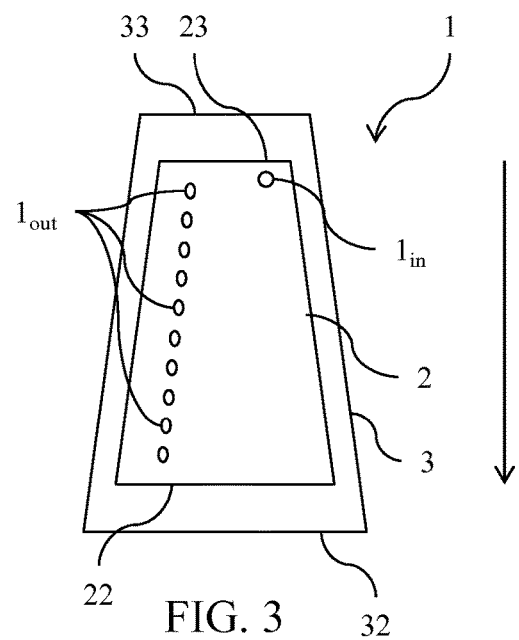
FIG. 3 is an illustration showing another embodiment of the cell with frustoconical inner and outer walls.

In one variant, both the outer face 21 of the inner wall 2 and the inner face 31 of the outer wall 3 can be frustoconical with the same apex angle, thus leaving a constant gap as well (see FIG. 3). The wider end of the inner wall 2 matches the wider end of the outer wall 3. In other words, the narrower end of the inner wall 2 matches the narrower end of the outer wall 3. In such a configuration, the shear rate increases from the narrower ends to the wider ends of the inner and outer walls 2, 3, thus creating a shear gradient (see arrow in FIG. 3).

Figure 4:
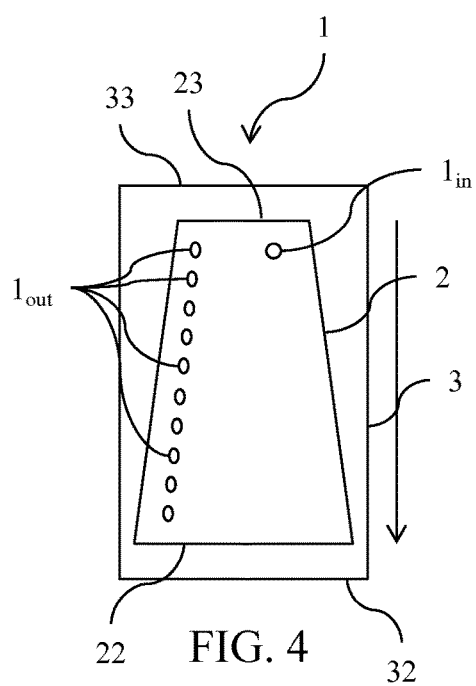
FIG. 4 is an illustration showing still another embodiment of the cell with a frustoconical inner wall and a cylindrical outer wall.

In another variant, the outer face 21 of the inner wall 2 can be frustoconical and the inner face 31 of the outer wall 3 can be cylindrical (see FIG. 4). Thus, the gap 4 between the inner wall 2 and the outer wall 3 is not constant. The shear rate gradually increases from the narrower end to the wider end of the inner wall 2 (see arrow in FIG. 4).

These two latter configurations can be for example advantageously used to separate different chiral species with same chirality (for example all being right-handed helices or all being left-handed helices) but with different size. Thus, a separation according to the size, from the smallest to the largest or the other way, along the longitudinal axis of the inner and outer walls 2, 3 is possible. In these configurations, the inlet $1_{in}$ is preferably situated at one end of the inner wall 2 and a plurality of outlets $1_{out}$ is provided along the inner wall 2 away from the inlet. For example, the inlet is situated at the narrower end of the inner wall 2 and the outlets longitudinally along the inner wall 2 towards its wider end.

Figure 5:
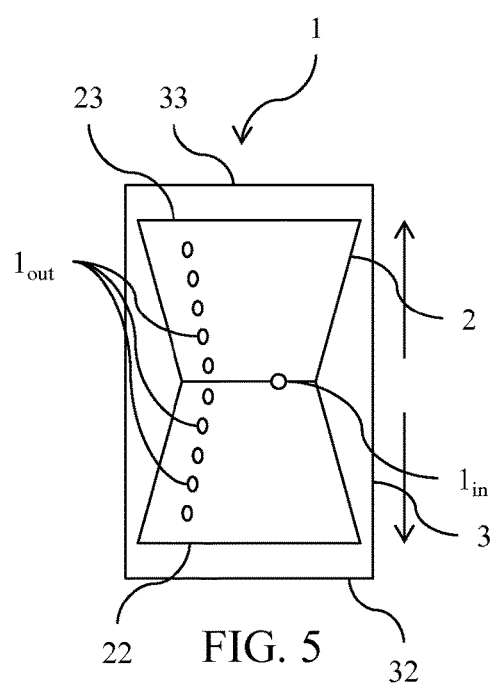
FIG. 5 is an illustration showing another embodiment of the cell with an inner wall, the outer face of which is formed by two frustoconical surface joined by their narrower end to one another.

Still in another variant, the outer wall 3 is cylindrical and the inner wall 2 has the shape of two, preferably identical, frustoconical solids joined to one another by their narrower ends (see FIG. 5). Thus the gap width is narrow at both ends of the cell and wider substantially in the middle thereof. Preferably, a central inlet $1_{in}$ is provided in the inner wall 2 at a location corresponding to where the two frustoconical solids joined together to form the inner wall 2 and two series of outlets $1_{out}$ are provided and distributed on both sides of the inlet up to the wider ends.

This configuration is particularly advantageous for example to separate different chiral species that can be sorted into two opposite types of chirality (e.g. left-handed helices and right-handed helices). When the mixture of these chiral species is introduced through the central inlet $1_{in}$, rotation of the outer wall 3 (optionally also the inner wall 2) causes the chiral species of one type (e.g. the right-handed ones) to migrate upwards and the chiral species of the other type (e.g. the left-handed ones) to migrate downwards. Thus a first separation occurs sorting the chiral species of one type from those of the other type (e.g. the right-handed ones from the left-handed ones). Then, as for the variants above, a second separation will occur for each of the chirality types according to the size of the chiral species.

For all these three latter configurations, there is a certain shear rate, more easily controlled by the rotation velocity of the outer wall 3, optionally also by the rotation velocity of the inner wall 2, at which for each specific chiral species (with definite chirality and size) the migration shift due to the Taylor-Couette flow will be balanced by diffusion. In such case, a plurality of vertical band corresponding to this specific chiral species will form inside the cell.

Other geometries for the inner and outer walls are possible, such as for example a frustoconical outer wall and a cylindrical inner wall.

Preferably, when the gap width G is constant between the outer face 21 of the inner wall 2 and the inner face 31 of the outer wall 3, it is set to be 100 nm to 10 mm More preferably, the gap width G is set to be 250 µm to 5 mm for micrometre-sized species and 100 nm to 250 µm for nanometre-sized species.

The outer wall 3 is generally closed at one of its longitudinal ends by a first end wall 32 that extends perpendicularly to the longitudinal axis of the outer wall 3. When the inner and outer walls 2, 3 are placed upright (i.e. their longitudinal axes A being vertical), the first end wall 32 forms the bottom closed part of the outer wall 3, thus becoming a bottom end wall. The other longitudinal end of the outer wall 3 may remain unclosed or closed by a top end wall 33.

When the outer wall 3 and the inner wall 2 are placed so that their longitudinal axes are horizontal, the first end wall 32, optionally the top end wall 33, becomes a lateral wall.

The length of the outer wall 3 is preferably 5 cm to 2 m and the diameter of the inner face thereof along its longitudinal axis is preferably 2 mm to 2 m.

It is possible to provide no base wall at neither ends of the inner wall 2 so that a through hole extends therethrough. It is also possible to provide at least one end wall 22, 23 in the same manner as for the outer wall 3. The length of the inner wall 2 is preferably 5 cm to 2 m and the diameter of the outer face thereof is preferably 1 mm to 2 m.

Preferably, the end of the inner wall 2 closer to the first end wall 32 at the outer wall 3 does not extend up to the first end wall 32. In other words, a space S remains between the first end wall 32 and the end of the inner wall 2 closer to the first end wall 32. The space width S is preferably set to be 100 nm to 10 mm.

When the outer wall 3 is closed at its both ends, it is preferably that neither one nor the other of the ends of the inner wall extends to the end walls closing the outer wall 3.

This has the advantage that the first end wall 32, and the other end wall 33 if any, plays substantially no driving role in the region of the walls' overlap. Indeed, the first end wall 32, and the other end wall 33 is any, moves at the same rotation velocity as the outer wall 3 thus influencing the liquid flow in its vicinity. If the corresponding end of the inner wall 2 extends down to the first end wall 32, there will not be any Taylor-Couette flow in a portion of the liquid at the bottom of the walls. The influence of the first end wall 32 on the liquid decreases along a direction collinear to the longitudinal axis and away from the first end wall 32. The same influence is present with the other end wall 33 when the outer wall 3 is closed at both ends thereof.

The inner and outer walls 2, 3 can be either upright, i.e. their longitudinal axes are vertical, or laid, i.e. their longitudinal axes are horizontal. The choice is free for chiral species of small size, usually smaller than 1 µm and generally for chiral species soluble in the liquid forming a solution or dispersible in the liquid to form a sol since gravity plays no role in the migration of the chiral species. However, for larger chiral species that sediment, the inner and outer walls are preferably upright. In such case, chiral species moving upwards will be slowed down by the gravity force, while those moving downward will be accelerated.

The device 1 further comprises:
- an actuator 5 for rotating the outer cylinder 3 in one direction of rotation so that in operation a Taylor-Couette flow is generated within the liquid; and
- a collector 6 for collecting at least one of the chiral species.

The collector 6 is connected to the outlet(s) $1_{out}$ of the cell. Optionally, there may be one collector 6 for each outlet $1_{out}$ or on one collector may be connected to a plurality of outlets $1_{out}$. For example, the device 1 comprises two collectors 6, 7 for collecting another one of the chiral species. They may be placed at opposite ends of the walls or at other advantageous location of the inner and/or outer walls 2, 3. Such configuration is particularly preferable when it is wished to collect two chiral species that travel along the longitudinal axis in opposite directions, e.g. a set of enantiomorphic species.

Generally speaking, the device 1 can comprise as many collectors as there are chiral species to be collected or collectors can be provided to collect more than one chiral species.

The device 1 may further comprise a command 8 connected to the actuator 5 of the outer wall 3 to set the rotation velocity of the outer wall 3. The command 8 may also be provided to command the actuator 5 of the outer wall 3 to change the rotation direction of the outer wall 3.

The device 1 may further comprise another actuator 9 for rotating the inner wall 2 in the same or opposite direction than the outer wall 3. In such case, the device 1 may further comprise a command 10 connected to the actuator 9 of the inner wall 2 to set the rotation velocity of the inner wall 2. The command 10 may also be provided to command the actuator 9 of the inner wall 2 to change the rotation direction of the inner wall 2.

The device 4 can also comprise a feeder 13 for feeding the cell with the liquid or a mixture of the liquid and the chiral species into the gap 4. The feeder 13 is connected to the inlet(s) $1_{in}$.

The device 1 can further comprise an electric field generator 11 for generating an electric field within the gap 4 for receiving the liquid. The electric field generator generates an electric field that is directed from the positively charged outer wall 3 towards the negatively charged inner wall 2. Thus, electric dipole of the chiral species undergoes a torque, leading to the alignment of the chiral species parallel to the electric field. If a gradient electric field in applied, it would be possible to control the radial position of the chiral species that move either towards to the inner wall 2 or the outer wall 3.

Alternatively or additionally, the device 1 can comprise a magnetic field generator 12 for generating a magnetic field within the gap 4 for receiving the liquid. The magnetic field generator generates a magnetic field that is directed from the positively charged outer wall 3 towards the negatively charged inner wall 2. Thus, magnetic dipole of the chiral species undergoes a torque, leading to the alignment of the chiral species parallel to the magnetic field. If a gradient magnetic field in applied, it would be possible to control the radial position of the chiral species that move either towards to the inner wall 2 or the outer wall 3.

The device 1 can also comprise a temperature controller 14 for controlling the temperature of the sell. The temperature controller 14 can be one of a Peltier type, heat-transfer fluid type and resistive type. The temperature controller 14 can be provided either to the inner wall 2, the outer wall 3 or both.

EXAMPLES

Nanometer-sized Species

As nanometre-sized species, 200 nm-long and 20 nm-wide silica nanometre-sized enantiomorphic twisted ribbons were used. Left-handed twisted ribbons are hereafter labelled S-ribbons and right-handed twisted ribbons R-ribbons. The ribbons are fluorescently labelled with sulforhodamine-B so that they can be imaged with a fluorescence microscopy. The nanometre-sized species were dispersed into water.

Taylor-Couette flow experiments on nanometre-sized enantiomorphic species were carried out with a Taylor-Couette cell with a rotating outer cylinder of radius of 1.45 mm and a stationary inner cylinder with a radius of 1.2 mm, both placed upright and coaxial to one another. The length of both cylinders was 36.8 mm. The temperature of the cell was set to 30° C. The liquid in which the nanometre-sized species were dispersed was water the dynamic viscosity of which is $0.798 \times 10^{-3}$ Pa·s at 30° C. Like all Newtonian fluids, water's viscosity does not depend on the shear rate used but only on the temperature.

The samples were subjected to several cycles with the outer cylinder turning clockwise and counter clockwise for several minutes before reaching a steady state. Then, the shift of the enantiomorphic species were recorded while rotating the outer cylinder in one direction (steady-state) during a first period of time of 30 seconds and in the opposite direction during a second period of time until a plateau is reached. This can be monitored thanks to the sulforhodamine-B labelling with the fluorescence signal increasing or decreasing depending on the object handedness and the rotation direction. All measurements were performed while rotating the outer cylinder at 5000 rpm resulting in a shear rate of about 2730 $s^{-1}$.

It could be observed that R-ribbons move downward when the outer cylinder is rotated clockwise and in the opposite direction, i.e. upward, when the outer cylinder is rotated counter clockwise. As for the S-ribbons, the motion direction is opposite, i.e. the S-ribbons move upward when the outer cylinder is rotated clockwise and downward when the outer cylinder is rotated counter clockwise.

Thus, a chiral resolution to separate R and S-ribbons using the method of the invention is possible.

Although the Péclet number was only 2.265, surprisingly, the longitudinal velocities of both the R and the S-ribbons were approximately 50 µm/s when the outer cylinder was rotated.

Supramolecular Chiral Assemblies

Either D-tartrate or L-tartrate, non-covalently bound to N1,N2-dihexadecyl-N1,N1,N2,N2-tetramethylethane-1,2-diaminium (a gemini surfactant), was used as chiral building block of the supramolecular chiral assemblies. D-tartrate and the gemini surfactant self-assemble into nanometre to micrometre long and 20 nm of diameter left-handed twisted ribbons hereafter S-ribbons, whereas L-tartrate and the gemini surfactant self-assemble into nanometre to micrometre long and 20 nm of diameter right-handed twisted ribbon hereafter D-ribbon.

Taylor-Couette cell with a rotating outer cylinder of radius of 1.45 mm and a stationary inner cylinder with a radius of 1.2 mm, both placed upright and coaxial to one another were used. The cylinders were each 36.8 mm long. All the results previously shown were obtained using water as a solvent whose dynamic viscosity is equal to $0.798 \times 10^{-3}$ Pa·s (at 30° C.). Like all Newtonian fluids, water's viscosity does not depend on the shear rate used but only on the temperature. The cell was thermostated at 30° C.

The samples were subjected to several cycles with the outer cylinder turning clockwise and counter clockwise for several minutes before reaching a steady state. Then, the shift of the enantiomorphic species were recorded while rotating the outer cylinder in one direction (steady-state) during a first period of time of 30 seconds and in the opposite direction during a second period of time until a plateau is reached. All measurements were performed while rotating the outer cylinder at 5000 rpm resulting in a shear rate of about 2730 $s^{-1}$.

It could be observed that R-ribbons move downward when the outer cylinder is rotated clockwise and in the opposite direction, i.e. upward, when the outer cylinder is rotated counter clockwise. As for the S-ribbons, the motion direction is opposite, i.e. the S-ribbons move upward when the outer cylinder is rotated clockwise and downward when the outer cylinder is rotated counter clockwise.

Thus, a chiral resolution to separate R and S-ribbons using the method of the invention is possible.

The Péclet number was 2.265, and the longitudinal velocities of both the R-ribbons and the S-ribbons were up to 50 µm/s.

Micrometer-sized Species

Figure 13:
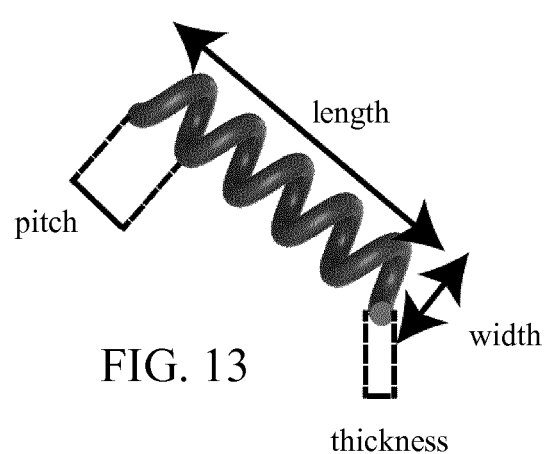
FIG. 13 illustrates schematically a helix-shaped micrometer-sized spiral obtained from *spirulina* blue-green algae (cyanobacteria).

Helix-shaped micrometer-sized spirals were obtained from *spirulina* blue-green algae (i.e., cyanobacteria) cultivated with regular liquid culture under light irradiation. The spirals (both right- and left-handed) were 150 µm long, 30 µm wide, 10.5 µm thick, and with a pitch of 20 µm (see FIG. 13).

Taylor-Couette flow experiments on these micrometer-sized enantiomorphic species were carried out with a Taylor-Couette cell with a rotating outer cylinder of inner radius of 1.45 mm and a stationary inner cylinder with an outer radius of 1.2 mm, both placed upright and coaxial to one another. The length of both cylinders was 36.8 mm. The temperature of the cell was set to 30° C. The liquid in which the micrometer-sized spirals were dispersed was water the dynamic viscosity of which is $0.798 \times 10^{-3}$ Pa·s at 30° C.

Experiments using either only right-handed spirals or left-handed spirals showed the following. Right-handed spirals moved upwards when the cylinder was rotated counter-clockwise and downwards when it was rotated clockwise. Oppositely, the left-handed spirals migrated upwards when the outer cylinder was rotated clockwise and downwards when it was rotated counter-clockwise. The autofluorescence of the spirals allowed them to be tracked using fluorescence microscopy. The average axial migration velocity, at outer cylinder rotation of 5000 rpm, was 0.3 mm $sec^{-1}$.

Experiments were performed using racemic mixtures of these micrometer-sized spirals at a right-handed:left-handed ratio of 1:1. First the spirals were concentrated at the top and bottom of the Couette cell by rotating the outer wall at 5000 rpm for 5 min., where the behaviour of the spirals was identical to the experiments with just one single entantiomorph (see above). Two concentrated plugs were formed at the two axial extremities of the cell. Next, the flow was suddenly reversed and the concentrated plugs moved in opposite direction meaning that the enantiomorph that was at the bottom of the cell moved to the top, whereas the enantiomorph located initially at the top moved to the bottom. Both concentrated plugs moved in opposite directions, crossed each other, and stopped moving when the extremities of the cell were reached. After one minute of flow reversal, the two enantiomorphs were fully spatially resolved over a centimetre distance indicating that chiral resolution can be achieved using a Taylor-Couette cell.

The invention claimed is:

1. A method for chiral resolution of chiral species contained in a liquid placed in a cell formed by an inner wall and an outer wall surrounding the inner wall over at least a portion of the inner wall, each of the outer and inner walls being a solid of revolution about a longitudinal axis, the outer and inner walls being coaxial to one another, the method comprising:
- rotating the outer wall in one direction of rotation with respect to the inner wall for generating a Taylor-Couette flow within the liquid; and
- collecting at least one of the chiral species.

2. The method of claim 1, further comprising collecting at least one of the other chiral species.

3. The method of claim 1, further comprising rotating the inner wall in the same or opposite direction as the outer wall.

4. The method of claim 1, wherein the liquid has a viscosity of $5 \times 10^{-5}$ Pas to $10^3$ Pas.

5. The method of claim 1, wherein the shear rate created within the gap is in average $1\ s^{-1}$ to $10^{12} s^{-1}$.

6. The method of claim 1, further comprising applying an electric field within the liquid.

7. The method of claim 1, further comprising applying a magnetic electric field within the liquid.

8. The method of claim 1, further comprising controlling the temperature within the cell.

* * * * *